United States Patent [19]

Bootman et al.

[11] Patent Number: 5,569,683

[45] Date of Patent: Oct. 29, 1996

[54] GEL COMPOSITIONS

[75] Inventors: Matthew W. Bootman, Medfield; Randall E. Adams, Billerica, both of Mass.

[73] Assignee: Thermedics, Inc., Woburn, Mass.

[21] Appl. No.: 445,644

[22] Filed: May 22, 1995

[51] Int. Cl.⁶ .............................. A61L 9/04; B01J 13/00
[52] U.S. Cl. .................... 523/102; 424/76.3; 424/76.4; 252/315.01; 428/905
[58] Field of Search .................. 523/102; 424/76.1, 424/76.2, 76.3, 76.4; 252/315.01; 428/905; 512/4

[56] References Cited

U.S. PATENT DOCUMENTS

| | | | |
|---|---|---|---|
| 3,145,514 | 8/1964 | Steffey | 239/36 |
| 3,269,278 | 8/1966 | Olstad | 156/157 |
| 3,462,329 | 8/1969 | Beyer | 428/40 |
| 3,685,734 | 8/1972 | Paciorek et al. | 239/56 |
| 4,064,645 | 12/1977 | Wood | 156/248 |
| 4,184,099 | 1/1980 | Lindauer et al. | 313/315 |
| 4,277,024 | 7/1981 | Spector | 239/36 |
| 4,283,011 | 8/1981 | Spector | 239/36 |
| 4,294,637 | 10/1981 | Rump | 156/157 |
| 4,359,358 | 11/1982 | Hattemer | 156/248 |
| 4,419,396 | 12/1983 | Sugimoto | 428/40 |
| 4,427,484 | 1/1984 | Cameron, Jr. et al. | 156/361 |
| 4,445,641 | 5/1984 | Baker et al. | 239/6 |
| 4,483,759 | 11/1984 | Szycher et al. | 204/159.24 |
| 4,587,129 | 5/1986 | Kliment | 426/534 |
| 4,606,956 | 8/1986 | Charbonneau et al. | 428/40 |
| 4,719,040 | 1/1988 | Traas et al. | 512/4 |
| 4,769,264 | 9/1988 | Dreger | 428/40 |
| 4,849,043 | 7/1989 | Instance | 156/227 |
| 4,874,129 | 10/1989 | DiSapio et al. | 239/36 |
| 4,880,690 | 11/1989 | Szycher et al. | 428/224 |
| 4,884,680 | 12/1989 | Israel et al. | 428/195 |
| 4,889,755 | 12/1989 | Charbonneau | 428/42 |
| 4,908,252 | 3/1990 | Carnahan et al. | 428/27 |
| 4,931,127 | 6/1990 | Matsumoto | 156/361 |
| 4,940,584 | 7/1990 | Tararuj et al. | 424/401 |
| 4,941,574 | 7/1990 | Meehan | 206/466 |
| 4,961,493 | 10/1990 | Kaihatsu | 206/0.5 |
| 4,987,161 | 1/1991 | Yamamoto | 523/102 |
| 5,071,704 | 12/1991 | Fischel-Ghodsian | 428/354 |
| 5,093,182 | 3/1992 | Ross | 428/195 |
| 5,161,688 | 11/1992 | Muchin . | |
| 5,391,420 | 2/1995 | Bootman et al. | 428/195 |

FOREIGN PATENT DOCUMENTS

| | | |
|---|---|---|
| 0431798 | 7/1987 | European Pat. Off. . |
| 0317658 | 11/1989 | European Pat. Off. . |

*Primary Examiner*—Paul R. Michl
*Assistant Examiner*—LaVonda R. DeWitt
*Attorney, Agent, or Firm*—Fish & Richardson P.C.

[57] ABSTRACT

A gel includes a multi-component scented mixture in which the components act in concert to create a perceived scent, disposed in a polymer matrix comprising the polymerization product of one or more ethylenically unsaturated monomers. The monomers are selected such that the gel (a) has sufficient mechanical integrity to retain its shape under ambient conditions and (b) releases the components of the scented mixture in a manner that substantially preserves the native scent of the mixture upon release.

14 Claims, No Drawings

GEL COMPOSITIONS

BACKGROUND OF THE INVENTION

This invention relates to polymer systems for releasing scented compositions.

Various polymer systems for releasing scented compositions, e.g., for use in fragrance samplers, have been proposed. For example, highly crosslinked gels (e.g., as described in Szycher et al., U.S. Pat. No. 4,880,690) have been used for this purpose. Such gels retain their shape under ambient conditions, and are adequate for certain scented compositions consisting of a single component. Often, however, the scented composition contains multiple components having different molecular sizes and volatilities that act together to give rise to the perceived scent. In the case of such multi-component scented compositions, it is important that all of the components be released in a manner that faithfully reproduces the native scent. Such release characteristics, however, are not realized with highly crosslinked gels, which trap some components within the polymer matrix, while releasing others.

SUMMARY OF THE INVENTION

In general, the invention features a gel that includes a multi-component scented mixture in which the components act in concert to create a perceived scent, disposed in a polymer matrix that includes the polymerization product of one or more ethylenically unsaturated monomers. The monomers are selected such that the gel (a) has sufficient mechanical integrity to retain its shape under ambient conditions and (b) releases the components of the scented mixture in a manner that substantially preserves the native scent of the mixture upon release.

In preferred embodiments, the multi-component scent mixture is a water-soluble or oil-soluble mixture. Examples of suitable mixtures include fragrance essences, food aroma essences, beverage essences, and deodorizing essences.

The gel is preferably the polymerization product of at least one mono-functional ethylenically unsaturated monomer, at least one multi-functional ethylenically unsaturated monomer (e.g., a di-functional ethylenically unsaturated monomer), or combination thereof. Examples of preferred monomers include acrylates, methacrylates, and combinations thereof.

The invention also features a method for preparing the above-described gels that includes (a) combining one or more ethylenically unsaturated monomers and a multi-component scented mixture in which the components act in concert to create a perceived scent to form a reaction mixture; and (b) exposing the reaction mixture to radiation to polymerize the monomers to form the gel. The radiation is preferably ultraviolet radiation.

As used herein:

"Native scent" refers to the scent of a composition in the absence of a polymer matrix.

"Ambient conditions" refer to the temperatures encountered during storage and sampling of the gel compositions.

A "gel" is a composition that is either physically crosslinked (by virtue of entangled polymer chains) or chemically crosslinked (by virtue of covalent bonds) such that it swells, but does not dissolve, in the presence of liquid.

An "essence" is the concentrated form of a scented material (e.g., a fragrance, food aroma, beverage, or deodorizing material).

A "water-soluble" scented composition is a composition that forms a homogeneous solution with water at 25° C. (as evidenced by the substantial absence of cloudiness and/or precipitation) at a concentration of 5 weight percent.

An "oil-soluble" scented composition is a composition that forms a homogeneous solution in ethanol at 25° C. (as evidenced by the substantial absence of cloudiness and/or precipitation) at a concentration of 5 weight percent.

A "mono-functional" reactant refers to a monomer having one carbon-carbon double bond available for polymerization.

A "multi-functional" reactant refers to a monomer having two or more carbon-carbon double bonds available for polymerization.

The invention provides gel compositions in which the release characteristics are tailored to yield an accurate reproduction of a multi-component scented composition. The compositions also retain their shape under ambient conditions, making them easy to handle and facilitating manufacture of samplers containing the gels. The ability to cure the gels by exposure to radiation further simplifies manufacture. Moreover, through judicious choice of monomers, the gels can be designed to accommodate either water-soluble or oil-soluble scented compositions.

Other features and advantages of the invention will be apparent from the following description of the preferred embodiments thereof, and from the claims.

DESCRIPTION OF THE PREFERRED EMBODIMENTS

Gels according to the invention feature a multi-component scented composition disposed in a polymer matrix that is the polymerization product of one or more ethylenically unsaturated monomers. Once formed, the gel continuously releases the scented composition until depleted to enable a consumer to sample the scent.

The gels are either physically crosslinked, chemically crosslinked, or feature a combination thereof. The degree of crosslinking is determined by the choice of the particular monomers that polymerize to form the polymer matrix (in particular, monomer functionality and, in the case of multi-functional monomers, the molecular weight between functional groups). It must be high enough to impart mechanical integrity to the gel under ambient conditions (e.g., such that the gel has the consistency of gelatin and can be readily handled), but not so high as to prevent or inhibit individual components of the scented composition from being released in order to preserve the native scent of the composition. In this way, a faithful reproduction of the scent upon release is ensured. The particular degree of crosslinking for any given gel, in turn, will depend on the specific scented composition being released (and the size and volatility of the individual components of the composition).

Another factor governing the release characteristics and composition of the gel relates to the compatibility of the polymer matrix with the multi-component scented composition being released. Where the solubility characteristics of matrix and scented composition are dissimilar, phase separation tends to occur, resulting in formation of dense, matrix-rich domains and scented composition-rich domains. This limits the amount of scented composition that can be incorporated in the matrix. Moreover, the matrix-rich domains effectively act as additional crosslinks, resulting in a gel that has less than optimum release characteristics.

Accordingly, it is preferred to select monomers which, when polymerized, yield polymers that are reasonably compatible with the particular scented composition being used such that significant phase separation is avoided. Thus, for example, hydrophilic monomers (e.g., containing hydrophilic pendant groups such as ionic, carboxyl, ether, and/or hydroxyl groups) are preferred in the case of water-soluble scented compositions, whereas hydrophobic monomers (e.g., containing hydrophobic pendant groups such as alkyl groups) are preferred for oil-soluble scented compositions.

Preferred monomers for use in gels according to the invention also have low odor (so that they do not interfere with the scented composition), low toxicity, and low volatility. In addition, the monomers are preferably polymerizable by exposure to radiation, e.g., ultraviolet or electron beam radiation (with ultraviolet radiation being preferred).

Examples of suitable mono-functional ethylenically unsaturated monomers include acrylamide, acrylic acid, hydroxyethylmethacrylate (HEMA), 2-ethoxyethyl acrylate, 2-phenoxyethyl acrylate, 2-(2-ethoxyethoxy)ethyl acrylate, t-butyl acrylamide, t-butyl acrylate, n-butyl acrylate, n-butyl acrylamide, 2-acrylamido-2-methylpropane sulfonic acid (AMPS) and the sodium salt thereof (NaAMPS), lauryl acrylate, lauryl methacrylate, stearyl acrylate, stearyl methacrylate, propylene glycol monoacrylate, caprolactone acrylate, nonylphenol acrylate, hexyl acrylate, isooctyl acrylate, carboxyethyl acrylate, isobornyl acrylate, polyether acrylate, nonylphenyl acrylate, ethoxylated nonylphenyl acrylate, and combinations thereof.

Examples of suitable di-functional ethylenically unsaturated monomers include ethylene glycol diacrylate, propylene glycol diacrylate, polyethylene glycol diacrylates (where the average molecular weight of the glycol moiety ranges from about 200 to about 600), 1,6-hexanediol diacrylate, methylene bi-acrylamide, 1,4-butanediol diacrylate, 1,3-butylene diacrylate, neopentyl glycol diacrylate, bisphenol diacrylate, and ethoxylated bisphenol diacrylate.

Examples of suitable multi-functional ethylenically unsaturated monomers having a functionality greater than two include trimethylolpropane triacrylate (TMPTA), ethoxylated trimethylolpropane triacrylate, propoxylated trimethylolpropane triacrylate, ethylenediaminetetraacetic acid tetraacrylate ester, pentaacrylate ester, silicone polyacrylate, silicone hexaacrylate, glyceryl triacrylate, propoxylated glyceryl triacrylate, pentaerythritol tetraacrylate, and di-trimethylolpropane tetraacrylate.

A variety of other materials may be incorporated in the gels as well. Such materials include antioxidants, viscosity modifiers (e.g., thickening agents), excipients, binders, adhesion promoters, emulsifiers, co-volatilizing agents, cure accelerators, pH modifiers, and preservatives (e.g., microbiocides and fungicides). Specific examples include alcohols (e.g., ethanol), glycols (e.g., propylene glycol, polyethylene glycol, and polypropylene glycol), water, butylated hydroxy toluene (BHT), tocopherols, aluminum trihydroxide, fumed silica, magnesium aluminum silicate, silica, cellulose and derivatives thereof (e.g., microcrystalline cellulose, hydroxyethyl cellulose, hydroxypropyl cellulose, carboxymethyl cellulose, cellulose acetate propionate, and ethyl cellulose), guar gum locust bean gum, plant hydrocolloids (e.g., alginate hydrocolloid), gum arabic, and water-soluble polymers (e.g., polyacrylic acid, poly-AMPS, poly-NaAMPS, and poly N-vinyl pyrrolidone), polypropylene-methyl glucose esters, and methyl gluceth polymers.

A wide variety of multi-component scented compositions are known and can be used in gels according to the invention. Examples include both fragrance essences and food aroma essences (e.g., vanilla oil, water-soluble coffee extracts, strawberry essence, and eucalyptus oil). The amount of scented composition in the gel may be up to about 60 percent by weight (based upon the total weight of the composition prior to polymerization), with amounts ranging from about 5% to about 50% (and, in particular, about 5% to about 25%) being preferred.

In the manufacture of one useful product in which the gels may be used, the gels are packaged to prevent the release of the scented composition until it is desired to sample the scent. An example of a preferred package is a hermetically sealed pouch or pouch label disclosed in Bootman et al., U.S. Pat. No. 5,391,420, hereby incorporated by reference. As disclosed therein, such samplers are manufactured according to a continuous process on a high speed line. The monomers, scented composition, any other additives, and a photoinitiator are mixed together in a single vessel, and then dispensed onto a continuously moving plastic sheet forming the backing of the pouch or pouch label. Examples of suitable photoinitiators are well-known and include benzophenonone, acetophenone, 4-morpholinobenzophenone, 4-methoxyacetophenone, diethoxyacetophenone, 2-hydroxy-2-methyl-l-phenyl-1-propanone, diphenyl (2,4,6-trimethylbenzoyl) phosphine oxide, 2,2-dimethoxy-2-phenylacetophenone, 2-methyl-l-(4 -methylthiophenyl)-2-morpholinopropanone-1,1-hydroxycyclohexylphenyl ketone, and combinations thereof. The composition is then exposed to ultraviolet radiation to cure the monomers and form the gel, and the gel is hermetically sealed between the backing and a top sheet member.

The invention will now be further described by way of the following examples.

EXAMPLES

Example 1

A formulation was prepared by combining the following ingredients:

| Ingredient | Weight Percentage |
| --- | --- |
| Vanilla Oil | 38.80 |
| Polyethylene glycol (400) diacrylate | 38.80 |
| Propylene glycol | 19.00 |
| Fumed silica | 1.94 |
| Butylated hydroxytoluene | 0.50 |
| 2-hydroxy-2-methyl-1-phenyl-1-propanone | 0.48 |
| Diphenyl(2,4,6-trimethylbenzoyl) phosphine oxide | 0.48 |
| TOTAL | 100.00 |

The formulation was coated onto a polyethylene terephthalate sheet at a thickness of between about 0.010 and 0.050 inch over an area of approximately one square inch. The sheet was then passed under a 300 watt ultraviolet lamp at a speed of 50 feet per minute to cure the formulation; the distance between the lamp and the sheet was about one inch. The resulting cured gel slabs were solid to the touch and continuously released fragrance until depletion.

Example 2

A gel was formed according to the procedure of Example 1 except that the formulation contained the following ingredients:

| Ingredient | Weight Percentage |
| --- | --- |
| Water-soluble coffee extract | 47.20 |
| NaAMPS | 23.50 |
| Water | 23.00 |
| Polyethylene glycol (400) diacrylate | 2.40 |
| Hydroxypropyl cellulose | 2.30 |
| 2-hydroxy-2-methyl-1-phenyl-1-propanone | 0.55 |
| Diphenyl(2,4,6-trimethylbenzoyl) phosphine oxide | |
| Butylated hydroxytoluene | 0.50 |
| TOTAL | 100.00 |

Example 3

A gel was formed according to the procedure of Example 1 except that the formulation contained the following ingredients:

| Ingredient | Percentage |
| --- | --- |
| Coty "Sand and Sable" fragrance oil concentrate | 50.00 |
| Ethoxylated nonylphenyl acrylate | 40.00 |
| 1,6-hexanediol diacrylate | 5.00 |
| Ethyl Cellulose | 3.00 |
| 2-hydroxy-2-methyl-1-phenyl-1-propanone | 2.00 |
| TOTAL | 100.00 |

Example 4

A gel was formed according to the procedure of Example 1 except that the formulation contained the following ingredients:

| Ingredient | Percentage |
| --- | --- |
| Water-soluble strawberry essence | 40.00 |
| NaAMPS | 26.00 |
| Polyethylene glycol (200) diacrylate | 5.00 |
| Water | 26.00 |
| Guar Gum | 0.50 |
| 2-hydroxy-2-methyl-1-phenyl-propanone | 2.00 |
| Butylated hydroxytoluene | 0.50 |
| TOTAL | 100.00 |

Example 5

A gel was formed according to the procedure of Example 1 except that the formulation contained the following ingredients:

| Ingredients | Percentage |
| --- | --- |
| Eucalyptus Oil | 40.00 |
| t-butyl acrylamide | 20.00 |
| Polyethylene glycol (200) diacrylate | 10.00 |
| Propoxylated trimethylolpropane triacrylate | 10.00 |
| Polypropylene glycol (4000) | 18.00 |
| 2-hydroxy-2-methyl-1-phenyl-propanone | 1.00 |
| Diphenyl(2,4,6-trimethylbenzoyl) phosphine oxide | 1.00 |
| TOTAL | 100.00 |

Example 6

A gel was formed according to the procedure of Example 1 except that the formulation contained the following ingredients:

| Ingredients | Percentage |
| --- | --- |
| Water-soluble Irish Cream Coffee Essence | 10.00 |
| NaAmps | 26.00 |
| Water | 26.00 |
| Propylene glycol | 25.00 |
| Polyethylene glycol (400) diacrylate | 10.00 |
| Hydroxypropyl cellulose | 1.50 |
| Diphenyl (2,4,6-trimethylbenzoyl) phosphine oxide | 1.00 |
| Butylated hydroxytoluene | 0.50 |
| TOTAL | 100.00 |

Other embodiments are within the following claims.

What is claimed is:

1. A gel comprising a multi-component scented mixture in which the components act in concert to create a perceived scent, disposed in a polymer matrix comprising the polymerization product of one or more ethylenically unsaturated monomers, said monomers being selected such that said gel (a) has sufficient mechanical integrity to retain its shape under ambient conditions, (b) releases the components of said scented mixture in a manner that substantially preserves the scent of said mixture upon release, and (c) is adapted for incorporation in a container manufactured according to a continuous process in a high speed line.

2. A gel according to claim 1 comprising a water-soluble multi-component scented mixture.

3. A gel according to claim 1 comprising an oil-soluble multi-component scented mixture.

4. A gel according to claim 1 comprising the polymerization product of at least one mono-functional ethylenically unsaturated monomer.

5. A gel according to claim 1 comprising the polymerization product of at least one multi-functional ethylenically unsaturated monomer.

6. A gel according to claim 1 comprising the polymerization product of at least one di-functional ethylenically unsaturated monomer.

7. A gel according to claim 1 comprising the polymerization product of at least one mono-functional ethylenically unsaturated monomer and at least one multi-functional ethylenically unsaturated monomer.

8. A gel according to claim 1 wherein said ethylenically unsaturated monomer comprises an acrylate, methacrylate, or combination thereof.

9. A gel according to claim 1 wherein said multi-component scented mixture comprises a fragrance essence.

10. A gel according to claim 1 wherein said multi-component scented mixture comprises a food aroma essence.

11. A gel according to claim 1 wherein said multi-component scented mixture comprises a beverage essence.

12. A gel according to claim 1 wherein said multi-component scented mixture comprises a deodorizing essence.

13. A method for preparing a gel composition comprising the steps of:

(a) combining one or more ethylenically unsaturated monomers and a multi-component scented mixture in which the components act in concert to create a perceived scent to form a reaction mixture;

(b) dispensing said reaction mixture onto a continuously moving sheet in a high speed manufacturing line; and (c) exposing said reaction mixture to radiation to polymerize said monomers to form a gel comprising said multi-component scented mixture disposed in a polymer matrix, said monomers being selected such that said gel (a) has sufficient mechanical integrity to retain its shape under ambient conditions, (b) releases the components of said scented mixture in a manner that substantially preserves the native scent of said mixture upon release, and (c) is adapted for incorporation in a container manufactured according to a continuous process in a high speed line.

14. A method according to claim 13 comprising exposing said reaction mixture to ultraviolet radiation.

\* \* \* \* \*